United States Patent [19]

St. John

[11] 4,418,565
[45] Dec. 6, 1983

[54] ULTRASONIC BUBBLE DETECTOR

[75] Inventor: Peter A. St. John, Adelphi, Md.

[73] Assignee: Baxter Travenol Laboratories, Inc., Deerfield, Ill.

[21] Appl. No.: 212,653

[22] Filed: Dec. 3, 1980

[51] Int. Cl.³ .......................................... G01N 29/02
[52] U.S. Cl. ..................................................... 73/19
[58] Field of Search ........................... 73/19, 61 R, 53; 128/663, 660, 214 E

[56] References Cited

U.S. PATENT DOCUMENTS

| | | | |
|---|---|---|---|
| 3,663,842 | 5/1972 | Miller | 73/644 |
| 3,921,622 | 11/1975 | Cole | 73/19 |
| 3,974,681 | 8/1976 | Namery | 73/19 |
| 4,015,464 | 4/1977 | Miller et al. | 73/61 R |
| 4,068,521 | 1/1978 | Cosentino et al. | 73/19 |
| 4,137,940 | 2/1979 | Faisandier | 128/214 E |

*Primary Examiner*—Stephen A. Kreitman

*Attorney, Agent, or Firm*—John P. Kirby, Jr.; Garrettson Ellis; Thomas A. Kmiotek

[57] ABSTRACT

Ultrasonic bubble detection apparatus utilizes a typically one-piece, rigid housing having a channel defined therein for receiving flow tubing in which bubbles are to be detected. First and second ultrasonic sending and receiving transducers are positioned on opposite sides of the channel, with an aperture communicating between each of the transducers and the channel, the aperture being filled with an elastomeric material capable of transmitting ultrasound energy between the channel and each transducer means. An air-containing slot may be positioned at the bottom of the channel to hinder the propagation of ultrasound energy through the housing from the first to the second transducer by a route other than one passing through the elastomeric material. Also, a novel shape for the apertures, and the elastomeric material filling them, is disclosed.

7 Claims, 3 Drawing Figures

ULTRASONIC BUBBLE DETECTOR

TECHNICAL FIELD

Ultrasonic bubble detection is utilized in many fields to determine the presence of bubbles in a line of flowing liquid under circumstances where visual or optical detection techniques are either undesired or unfeasible.

In particular, there exists a growing number of technologies relating to the automated processing of blood, blood components, or parenteral solutions. In particular, there is a growing technology relating to the pumped administration of parenteral solutions to a patient, where a bubble detector may be needed to automatically shut the defice off when a bubble is detected, since it is imperative that the patient be protected from the accidental infusion of air bubbles. Likewise, in hemodialysis, blood oxygenation, or blood component collection, where blood or blood components are withdrawn from a patient, processed in various ways, and returned to the patient, automated detection of bubbles may be necessary to shut the apparatus off in the event of their detection so that air bubbles are not readministered to the patient or donor.

BACKGROUND ART

In Cosentino U.S. Pat. No. 4,068,521 an ultrasonic air and blood foam detector is disclosed, made of a two-piece housing which is clamped together about tubing in which bubbles are to be ultrasonically detected.

Cole U.S. Pat. No. 3,921,622 also discloses a two-piece housing for an ultrasonic bubble detector in which tubing is installed in the housing, and the two pieces of the housing are brought together to bring a pair of ultrasonic transducers into contact with the tubing.

In Miller U.S. Pat. No. 3,663,842, an ultrasonic probe is disclosed, having a composite matrix material as a device for coupling the signals from piezoelectric elements to the desired material for testing, in which the composite matrix may contain an elasotomeric component.

One problem with the construction of ultrasonic bubble detectors is that ultrasonic energy tends to find its way through the respective housings from one transducer to the other without passing through the tubing through which bubbles may pass. This provides an undesirable background noise level, which reduces the sensitivity of the apparatus.

Accordingly, it has been generally preferred for the various two-piece housings utilized in ultrasonic detectors to have an air gap between them, to block the transmission of ultrasonic energy by routes other than the desired route passing through the liquid-filled conduit to be monitored.

The existence of transmissions of ultrasound energy by routes other than that desired between the two transducers has tended to lead those skilled in the art away from the use of one-piece housings in accordance with this invention. Under the prior art conditions of use, such a one-piece housing could have a very high background noise, due to the transmission of ultrasound energy directly in the housing from one transducer to another.

It has also been found that when piezoelectric transducer sending and receiving crystals are of a thickness selected to be resonant at a frequency on the order of 1 to 3 MHz, the resulting ultrasonic vibration exhibits substantial advantages over lower frequency sonic systems, in that such high frequency sonic vibrations are very poorly coupled with air. Accordingly, the presence of a bubble can cause a very major change in the sensing signal, so that the ultrasonic bubble detection systems may have substantially increased sensitivity.

DISCLOSURE OF INVENTION

In accordance with this invention, an ultrasonic bubble detection apparatus may comprise a one-piece, rigid housing, having a channel defined in the one-piece housing for receiving flow tubing in which bubbles are to be detected.

First ultrasonic sending transducer means may be positioned in the housing on one side of the channel, while second ultrasonic receiving transducer means is positioned on the other side of the channel. Apertures are provided in the housing to respectively communicate between each of the first and second transducer means and the channel. The apertures are filled with an elastomeric material capable of transmitting ultrasound energy between the channel and each transducer means, while electric leads communicate from each transducer means to the exterior of the housing, for appropriate control and read-out purposes, which may be generally conventional.

In accordance with this invention, an added air-containing slot may be positioned in the bottom of the channel, being of a width too small to contain the tubing positioned within the channel, and being of a depth extending at least below the lower edge of each of the transducer means. The result of this is to hinder the propagation of ultrasound energy through the housing from the first to the second transducer by a route other than one passing through the elastomeric material, since the air barrier in the slot greatly attenuates the ultrasonic vibrations, preventing them from reaching the second, receiving transducer means by a route passing entirely through the material of the housing.

Thus, substantially all of the ultrasonic vibrations which do reach the receiving transducer get there by the desired route through the elastomeric material and tubing inserted in the channel in contact with the elastomeric material, to provide transmission of ultrasound energy between the first and second transducers.

Transmission of the ultrasound energy is significantly altered by the presence of a bubble in the tubing, when compared with the tubing completely filled with liquid. This significant alteration may be electronically detected, and a conventional electronic system may be provided to shut off the apparatus, actuate an alarm, or perform any other function as may be desired upon the detection of a bubble.

The transducer means utilized herein may preferably be a conventional piezoelectric crystal disc of a thickness selected to be resonant in the range of 1 to 3 MHz, and specifically about 2.25 MHz. As is well known, such crystals may be excited to oscillate in a thickness mode by a radio frequency signal applied to the sides of the disc. The resulting mechanical motion of the crystal may then be coupled by the elastomeric material described above to the side of flexible tubing positioned in the channel, which tubing may be part of a set for the pumped infusion of liquids, for example, or any other fluid flow conduit. On the opposite side of the channel and the tubing therein, the other section of elastomeric material described above serves as a coupling between the channel and the receiving transducer, being attached to the receiving transducer which may also be a similar piezoelectric crystal. Ultrasonic vibrations set up by the sending transducer pass through the elastomeric material and the generally liquid-filled tubing, to strike the receiving transducer, which proceeds to vibrate in sympathy with the ultrasonic vibrations to produce an alternating current potential proportional to the relative degree of vibratory coupling of the two transducer units.

When air is introduced to the area between the transducers, and specifically inside of the flexible tubing the degree of coupling of sound energy abruptly drops, and the output voltage of the receiving transducer drops accordingly.

Thus, bubbles can be detected, even though the tubing or the liquid contained therein is opaque and, as stated above, in particularly the preferred frequency range the sensitivity of the system can be very high, since it is possible to effectively insulate by means of the air-containing slot the second receiving transducer from any leakage of ultrasonic vibrations. This is so despite the fact that a one-piece, rigid housing is utilized, which may be a great convenience of construction and also of use.

Despite the characterization of the housing of this invention as "one-piece" it may be desired to put a lid or the like over the one-piece housing while in operation. This does not change its character as a one-piece housing, since both of the transducers are carried by the one-piece housing, being separated by the channel defined therein.

It is also generally preferred for the elastomeric material filling the aperture means on both sides of the channel to be made of silicone rubber which has a low filler loading, and also which preferably has a relatively low temperature flexibility. An example of a suitable silicone rubber for purposes of this invention is General Electric RTV 118, a translucent silicone rubber, indicative of low filler loading, and having a relatively low temperature flexibility. Also, formulations containing significant amounts of phenylmethylsiloxane units having relatively low filler loading may exhibit the desired low temperature flexibility, and may be particularly suitable for use herein.

It is, of course, desirable for the elastomeric material to be of maximum transmissivity to the particular ultrasound energy utilized.

The one-piece, rigid housing may, for example, be made of a glass-filled polytetrafluoroethylene (sold under the tradename Teflon). Such material turns out to be very nontransmissive to ultrasound energy on the order of 2.25 MHz, and thus is particularly desirable for use herein.

The aperture means preferably comprises a pair of apertures each on one side of the channel for the tubing, with the apertures respectively communicating between each of the first and second transducer means and the channel. Each aperture, and the elastomeric material filling each aperture, may preferably be of a shape comprising a disc portion adjacent each of the first and second transducer means, with each disc portion of elastomeric material adhered at its outer face to a face of the adjoining transducer means, for example, by a conventional adhesive or the like.

Each aperture, and the elastomeric material carried thereon, also may comprise an elongated projection extending from the channel to the side of each disc portion opposed to the adjacent transducer means. The elongated projection of elastomeric material is preferably integral with the adjacent disc portion of elastomeric material. As the result of this, an integral path of elastomeric material communicates directly from each transducer to the channel, with the elongated projection of elastomeric material extending inwardly of the channel to a degree sufficient to assure firm contact with flow tubing positioned in the channel. Thus, vibrational energy generated in the first transducer means may be conveyed to tubing in the channel through elastomeric material in one aperture, and then transported through the tubing and the elastomeric material in the other aperture to the second, receiver transducer, with reduced attenuation of sound.

The elongated projections may be proportioned in cross section to be of essentially the diameter of the tubing to be monitored. Specifically, each elongated projection of the apertures on the opposite sides of the channel, and the elastomeric material therein may be of generally oval cross section with the longest axis of the oval cross section being positioned to be essentially parallel to the axis of the flow tubing positioned in the channel. This provides an improvement in the transmission of sound energy through the flow tubing.

Similarly, each elongated projection is not positioned in coaxial manner with the disc portion of each aperture, but instead is spaced toward the outer portion of the slot from the axis of each disc portion.

Also, each of the sending and receiving transducer means may be positioned in a chamber defined by the housing and held in the chamber by annular retention means which press against only the peripheral portions of the respective transducer means, so that outwardly-facing central portions of the transducer means face an open space. This provides a significant improvement in the generation and receiving of ultrasonic energy between the two transducers.

DESCRIPTION OF SPECIFIC EMBODIMENT

Figure 1:
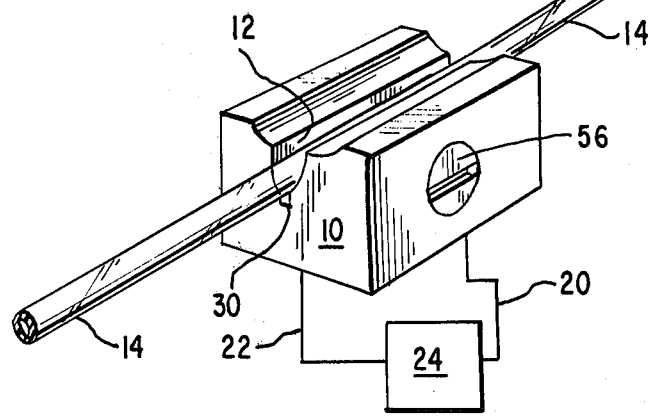
FIG. 1 is a perspective view of the ultrasonic bubble detection apparatus of this invention, shown in partly schematic form.

Referring to the drawings, an ultrasonic bubble detection apparatus is disclosed comprising preferably a one-piece, rigid housing 10 which may be made of glass-filled Teflon as stated above, and having an open channel 12 which is defined in the one-piece housing for receiving flow tubing 14 in which bubbles are to be detected. For example, flow tubing 14 may be part of a parenteral solution administration set connected to a pump for administering precise volumes of parenteral solution over a period of time. In such circumstances a bubble detection system is particularly desirable as a safety measure to prevent the accidental infusion of air bubbles in the patient.

A first ultrasonic sending transducer 16 may be in the form of a disc of piezoelectric material, for example of ½ inch diameter and 0.035 inch thickness, and being made of a commercially available material: Golton G 1500 sold by the Golton Corporation, being a mixture of lead zirconate and barium titanate.

Second ultrasonic receiving transducer means 18 may be a similar transducer of similar dimensions, although it is not necessarily critical for the transducer to be of identical shape.

Electric leads 20, 22 pass through apertures in housing 10 and communicate with the sides of transducer discs 16, 18 respectively. Thus an RF signal may be applied to the side of transducer 16 to cause it to oscillate in thickness mode with a resonance of 2.25 MHz, for example. This ultrasonic energy is then transmitted to the receiver transducer which oscillates in sympathy therewith, and a consequent RF signal is generated in lead 22 for sensing.

Conventional electronics such as a commercial electronic system 24 with little or no modification may be utilized to provide the RF signal to lead 20, and to sense the output from lead 22, to sound an alarm and shut off the operation of an infusion pump as may be desired when the output from lead 22 indicates the presence of a bubble in tube 14.

One-piece housing 10 may be made of a single, molded piece for ease of manufacture and low cost.

Apertures are provided communicating between the first and second transducers 16, 18 and channel 12, with each aperture being filled with an elastomeric member 26, 28. Each elastomeric member 26, 28 is a single piece of silicone rubber, preferably of the type described previously, and capable of transmitting ultrasound energy between channel 12 and each transducer 16, 18.

An air-containing slot 30 typically extends the entire length of channel 12 being positioned in the bottom of channel 12 and of a width as shown which is too small to contain tubing 14 positioned within the channel.

The depth of slot 30 preferably is sufficient to cause the slot to extend below the lower edge 32 of each transducer means 26, 28. Typically slot 30 extends at least 0.05 inch lower than the lower edges 32 of the transducers.

The effect of this is to hinder the propagation of ultrasound energy from transducer 26 through housing 10 to second transducer 28 by a route other than the one passing through the elastomer members 26, 28, to reduce ultrasound background noise sensed by transducer 18 for increased sensitivity of operation. It has been found that the existence of such a slot 30, particularly in the situation when ultrasound of frequencies of at least 1 MHz is used, permits the effective suppression of background noise, despite the fact that a one-piece housing 10 is utilized containing both transducers, which permits by this invention the use of a convenient and inexpensive one-piece housing without the disadvantages previously encountered with the use of such housing.

Each of silicone rubber members 26, 28, residing in their corresponding apertures, are of a shape comprising a disc portion 34, 36 which is positioned adjacent its respective transducer 16, 18 and typically glued thereto in face-to-face relationship by a conventional adhesive, for example, an RTV silicone elastomer such as General Electric 118.

Furthermore, each elastomeric member 26, 28 further comprises an elongated projection 38, 40 extending from channel 12 to the side of each disc portion 34, 36 opposed to its adjacent transducer means 16, 18. Preferably, as stated above, the elongated projections 38, 40 are integrally molded with their adjacent disc portions 34, 36.

As the result of this, a bridging path of elastomeric material which is transmissive to ultrasound communicates directly from each transducer 16, 18 to channel 12. Each elongated projection 38, 40 extends inwardly of channel 12 to a degree sufficient to assure firm contact with flow tubing 14 positioned in the channel.

Figure 3:
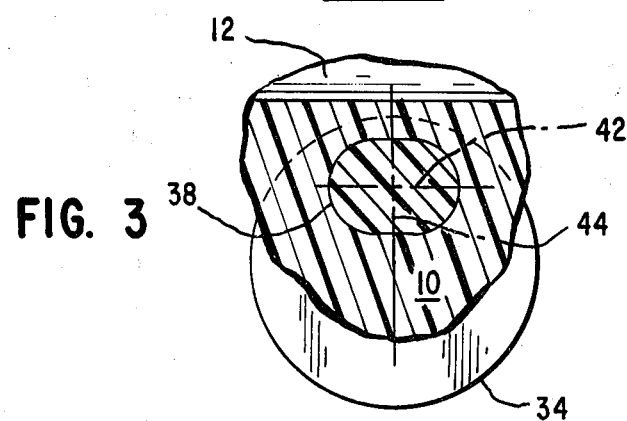
FIG. 3 is a fragmentary sectional view taken along line 3—3 of FIG. 2.

As shown in FIG. 3, elongated projection 38 may be of generally oval cross section, with its longest axis 42 being positioned to be essentially parallel to the axis of flow tubing 14 positioned in channel 12. At the same time minor axis 44 of the cross section of elongated projection 38 may be proportioned to be of such a width that essentially the entire end of projecting member 38 is in complete and maximum contact with the surface of tube 14. If desired, the outer end of projecting member 38 may be concave to fit with tube 14, or alternatively, it may be flat, with minor axis 44 being wide enough that the entire surface area of the end of member 38 is in contact with tube 14, with little or no peripheral area of member 38 being spaced from the tube. This provides improved ultrasound transmission capability, with minimum ultrasound attenuation during transmission.

The cross sectional shape of elongated projection 40 may be similar to that of projection 38.

Figure 2:
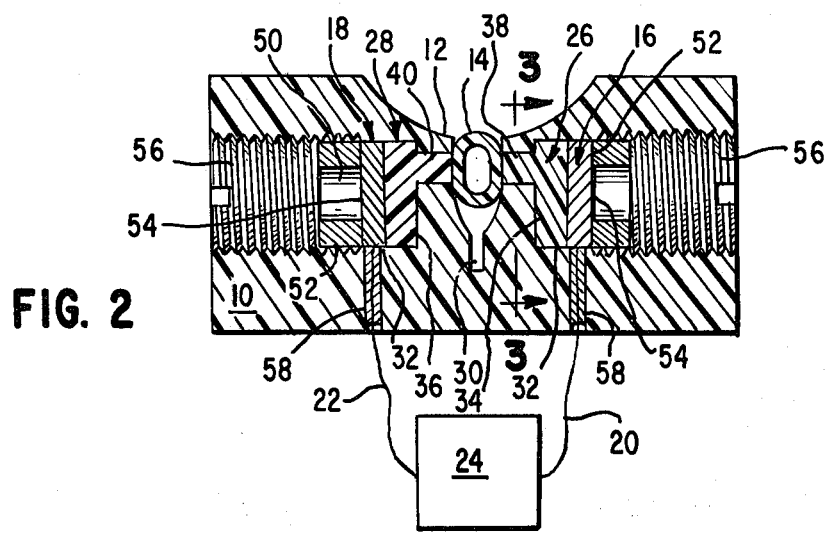
FIG. 2 is a transverse sectional view of the structure of FIG. 1.

Also, as shown in FIG. 2 projections 38, 40 are not in coaxial relation with disc portions 34, 36. Instead, projections 34, 36 are spaced toward the outer portion 46 of slot 12 from the axis of each disc portion 34, 36.

Transducers 16, 18 are respectively positioned in chambers 48, 50 by a series of $\frac{1}{2}$ inch washers or a single relatively thick washer 52 as may be desired, so that each transducer 16, 18 is held in its respective chamber by annular retention and pressure against only the peripheral portions of the respective transducer means. Hence, the outwardly-facing central portions 54 of the transducers may face an open space as shown.

Washers 52 are then retained in respective apertures 48, 50 by threaded plugs 56, which are threaded in screw threads defined in the outer portions of chambers 48, 50 for firm retention of the unit and sealing thereof. The apertures for leads 20, 22 may be filled with a potting compound 58, if desired, for further protection and sealing of the system.

Accordingly, as liquid passes through tubing 14, and ultrasound energy at a frequency of 2.25 MHz is propagated by transducer 16, the ultrasound energy is transmitted with relatively little attenuation through elastomer member 26, liquid-filled tubing 14, and elastomer member 28, to be received by transducer 18, resulting in an electrical output in lead 22 which communicates with the conventional electronic circuitry 24.

When a bubble in tubing 14 passes between elastomer members 26, 28, the intensity of the ultrasound transmitted between the two transducers is sharply decreased for an instant, which fact is duly reflected by the output of lead 22. This is interpreted by the electronic system 24 as a positive indication of the presence of a bubble, and the desired remedial action may be automatically initiated by electronic system 24, for example shutoff of the system and triggering of an alarm. By way of modification of the invention of this application, by varying the sonic path lengths between the transducers, it is possible to modify the standing waves between the transducers so that they tend to cancel each other as sensed at the second receiving transducer. In this circumstance, an air bubble can generate a net increase in the sonic coupling between the transducers, if such is desired rather than a decrease in sonic coupling specifically described herein.

It may also be added that the use of a thickness mode oscillator as the transducer means permits the transducer crystals to vary in diameter without affecting the resonant frequency. However, other oscillators may be used as an equivalent to the specific transducers described herein.

An advantage of the invention of this application is that the single-unit housing specifically disclosed herein eliminates the need for mechanically moving parts. Thus the transducer crystals and related parts may be held in precise, spaced relationship.

The above has been offered for illustrative purposes only, and is not intended to limit the scope of the invention of this application, which is as defined in the claims.

That which is claimed is:

1. In ultrasonic bubble detection apparatus, a one-piece, rigid housing made of glass-filled polytetrafluoroethylene, a channel defined in the one-piece housing for receiving flow tubing in which bubbles are to be detected; first ultrasonic sending transducer means positioned in said housing on one side of the channel; second ultrasonic receiving transducer means positioned on the other side of said channel, said sending and receiving transducer means being of the type for respectively sending and receiving ultrasound energy at a frequency of 1 to 3 MHz; aperture means respectively communicating between each of said first and second transducer means and said channel, said aperture means being filled with an elastomeric material capable of transmitting ultrasound energy between said channel and each transducer means; electric lead means communicating from each transducer means to the exterior of said housing, and added air-containing slot means positioned in the bottom of said channel of a width too small to contain the tubing positioned within said channel and being of a depth extending below the lower edge of each of said transducer means, to hinder the propagation of ultrasound energy through said housing from the first to the second transducer by a route other than one passing through said elastomeric material, whereby tubing inserted in said channel may be in contact with said elastomeric material to provide transmission of ultrasound energy between the first and second transducers, which transmission of ultrasound energy is significantly altered by the presence of a bubble in the tubing, when compared with said tubing completely filled with liquid.

2. The ultrasonic bubble detection apparatus of claim 1 in which said elastomeric material is translucent silicone rubber.

3. The ultrasonic bubble detection apparatus of claim 1 in which each aperture means comprises a pair of apertures respectively communicating between each of the first and second transducer means and said channel; each aperture, and the elastomeric material filling each aperture, being of a shape comprising a disc portion adjacent each of said first and second transducer means, each disc portion of elastomeric material being adhered at its outer face to a face of the adjoining transducer means, each aperture, and the elastomeric material carried therein, also comprising an elongated projection extending from said channel to the side of each disc portion opposed to the adjacent transducer means, said elongated projection of elastomeric material being integral with its adjacent disc portion of elastomeric material, whereby a bridging path of elastomeric material communicates directly from each transducer to said channel, extending inwardly of said channel to a degree sufficient to assure firm contact with flow tubing positioned in said channel.

4. The ultrasonic bubble detection apparatus of claim 1 in which each of said sending and receiving transducer means are positioned in a chamber defined by said housing, and held in said chamber by annular retention means which press against only the peripheral portions of the respective transducer means, so that outwardly-facing central portions of said transducer means face an open space.

5. In ultrasonic bubble detection apparatus, a channel defined in the one-piece housing for receiving flow tubing in which bubbles are to be detected; first ultrasonic sending transducer means positioned in said housing on one side of said channel; second ultrasonic receiving transducer means positioned on the other side of said channel; aperture means respectively communicating between each of said first and second transducer means and said channel, said aperture means being filled with an elastomeric material capable of transmitting ultrasound energy between said channel and each transducer means; said housing having an air-containing slot positioned in the bottom of said channel of a width too small to contain the tubing positioned within said channel and being of a depth extending below the lower edge of each of said transducer means, to hinder the propagation of ultrasound energy through said housing from the first to the second transducer by a route other than one passing through said elastomeric material; each aperture means comprising a pair of apertures communicating between each of the first and second transducer means and said channel; the elastomeric material filling each aperture comprising a shape comprising a disk portion adjacent each of said first and second transducer means, each disk portion of elastomeric material being adhered at its outer face to a face of the adjoining transducer means, the elastomeric material carried in each aperture also comprising an elongated projection extending from said channel to the side of each disk portion opposed to the adjacent transducer means, said elongated projection of elastomeric material being integral with its adjacent disk portion of elastomeric material, whereby a bridging path of elastomeric material communicates directly from each transducer to said channel, extending inwardly of said channel to a degree sufficient to assure firm contact with flow tubing positioned in said channel; electric lead means communicating from each transducer means to the exterior of said housing, whereby tubing inserted in said channel may be in contact with said elastomeric material to provide transmission of ultrasound energy between the first and second transducers, which transmission of ultrasound energy is significantly altered by the presence of a bubble in the tubing, when compared with said tubing completely filled with liquid.

6. The ultrasonic bubble detection apparatus of claim 5 in which each elongated projection of the apertures on opposite sides of the channel, and the elastomeric material therein, is of generally oval cross section, with the longest axis of said oval cross section being positioned to be essentially parallel to the axis of flow tubing positioned in said channel.

7. The ultrasonic bubble detection apparatus of claim 5 in which said elongated projection of each aperture means is spaced toward the outer portion of said slot from the axis of each disc portion of said aperture means.

* * * * *